United States Patent [19]

Fowlkes

[11] Patent Number: 5,074,967
[45] Date of Patent: Dec. 24, 1991

[54] SEPARATION OF METHOXYISOPROPYLAMINE FROM METHOXYISOPROPYLAMINE-WATER AZEOTROPE

[75] Inventor: Robert L. Fowlkes, Milton, Fla.

[73] Assignee: Air Products and Chemicals, Inc., Allentown, Pa.

[21] Appl. No.: 681,847

[22] Filed: Apr. 8, 1991

[51] Int. Cl.$^5$ .................... B01D 3/14; C07C 209/84; C07C 209/86
[52] U.S. Cl. ........................................ 203/14; 203/75; 203/77; 203/78; 203/80; 564/497
[58] Field of Search .................. 203/14, 75, 77, 78, 203/80, 74; 564/497, 499

[56] References Cited
U.S. PATENT DOCUMENTS

| 2,512,584 | 6/1950 | Smith | 564/497 |
|---|---|---|---|
| 3,433,788 | 3/1969 | Somekh et al. | 544/106 |
| 4,283,254 | 8/1981 | Binau et al. | 564/497 |
| 4,407,703 | 10/1983 | Featherstone | 203/43 |
| 4,543,163 | 9/1985 | Stamerjohn et al. | 203/77 |
| 4,798,910 | 1/1989 | Herrin | 564/497 |
| 4,868,335 | 9/1989 | Fowlkes et al. | 564/497 |

FOREIGN PATENT DOCUMENTS

| 0142539 | 7/1980 | Fed. Rep. of Germany | 564/497 |
|---|---|---|---|
| 0421486 | 12/1934 | United Kingdom | 564/499 |
| 2113211 | 8/1983 | United Kingdom | 564/497 |

Primary Examiner—Virginia Monoharan
Attorney, Agent, or Firm—Russell L. Brewer; James C. Simmons; William F. Marsh

[57] ABSTRACT

A process for the recovery of methoxyisopropylamine from the reaction of methoxyisopropanol and ammonia under amination conditions. Water is produced as a byproduct and in the distillation separation an azeotrope is formed which includes about 14% water and 86% methoxyisopropylamine. The improvement for enhancing separation of the azeotrope includes initially distilling the mixture of methoxyisopropylamine, methoxyisopropanol and water under sufficient elevated pressure wherein an azeotrope of water and methoxyisopropylamine overhead and an essentially water free bottoms of methoxyisopropylamine and methoxyisopropanol are formed. The overhead from this initial distillation column is charged to a second distillation column operated at reduced pressure wherein an organic free bottoms containing primarily water is obtained. The bottoms from the elevated pressure distillation column is fractionated in a product column and product methoxyisopropylamine is recovered as an overhead and methoxyisopropanol as a bottoms.

The overheads from the lower pressure distillation column is returned to the elevated pressure column and all of the methoxyisopropylamine is recovered.

6 Claims, 1 Drawing Sheet

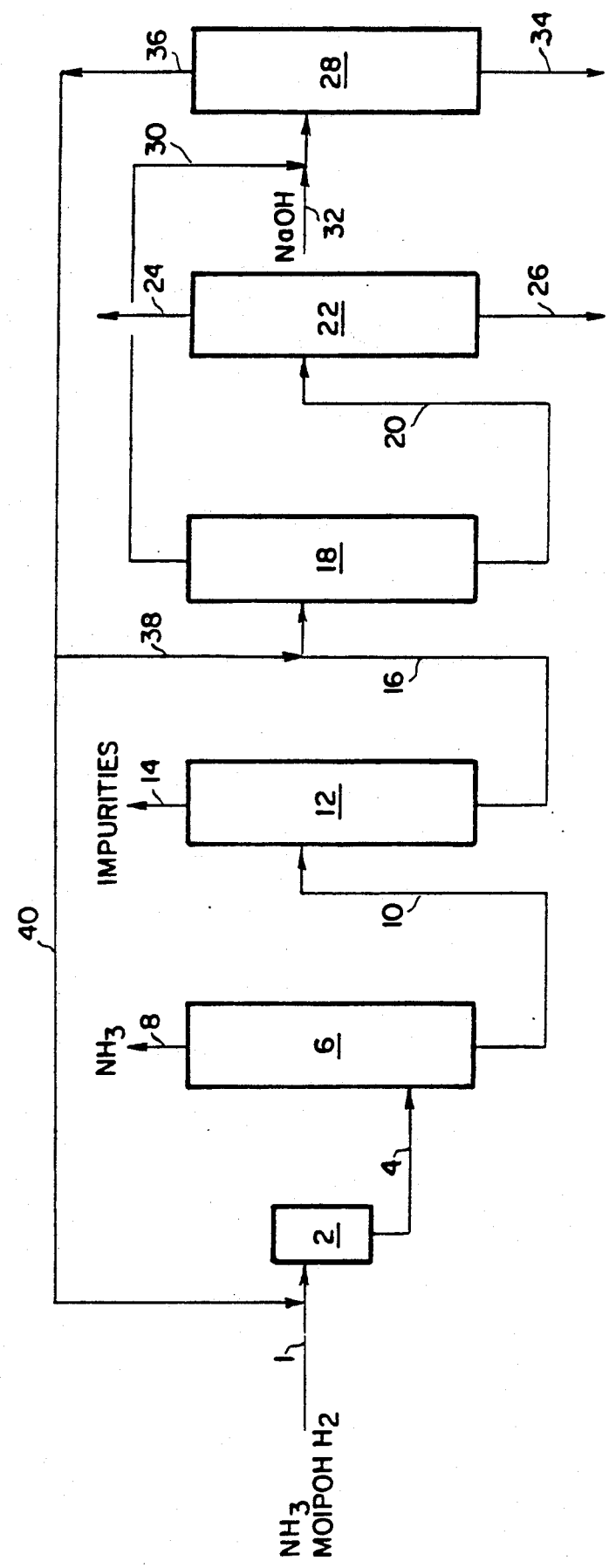

SEPARATION OF METHOXYISOPROPYLAMINE FROM METHOXYISOPROPYLAMINE-WATER AZEOTROPE

TECHNICAL FIELD

This invention related to the separation of methoxyisopropylamine from methoxyisopropylamine-water azeotrope.

BACKGROUND OF THE INVENTION

In the conventional manufacture of methoxyisopropylamine, methoxyisopropanol is contacted with ammonia in the presence of a catalyst under amination conditions to produce methoxyisopropylamine and by-product water. One of the problems associated with the recovery of the methoxyisopropylamine from the reaction mixture is that an azeotrope consisting of about 14% water and 86% methoxyisopropylamine is formed. The methoxyisopropylamine-water azeotrope is extremely difficult to separate and therefore produce a methoxyisopropylamine product which is essentially anhydrous. eg., less than about 1% water. Any residual water in the methoxyisopropylamine tends to affect its usefulness as a reactant in many chemical reactions.

The following patents illustrate various approaches to the separation of amine-water azeotropes.

U.S. Pat. No. 4,868,335 discloses the recovery of mono-n-hexylamine from a mono-n-hexylamine-water azeotrope. To effect separation. the azeotrope is contacted with di-n-hexylamine or a mixture of di-n-hexylamine and tri-n-hexylamine. The di-n-hexylamine forms a lower boiling azeotrope with water and is removed by distillation. The organic phase then can be separated from the aqueous phase by decanting.

U.S. Pat. No. 3,433,788 discloses a process for recovering amines from aqueous solutions by solvent treatment and distillation. In particular the invention pertained to processes for the recovery of morpholine from aqueous solutions wherein the N-alkylmorpholines and some other amines form an azeotrope with water which could not be separated. Dewatering techniques involving the addition of sodium hydroxide were suggested, however, it was pointed out that the sodium hydroxide had to be recovered and that large amounts of water had to be removed by distillation. Ethyl ether was disclosed as being an extractant for morpholine but was unsatisfactory because of losses due to the high volatility of ethyl ether. The patentees suggested the utilization of an inert, water-immiscible, selective liquid organic solvent as an extractant. Specifically the extractants listed were organic vehicles which were inert to the amine and had a boiling point higher than the amine compound. Solvents included aliphatic alcohols, saturated aliphatic hydrocarbons, halogenated aliphatic hydrocarbons, saturated ketones, ester derivatives of ethyl and diethyleneglycol, alkylphosphoric acids, alkylcarboxylic acids, and alkylamines.

U.S. Pat. No. 4,407,703 discloses an amine separation process wherein isomers of alkylamines are separated into their constituent components. The process involves first distilling the mixture and recovering at least one pure component. The remainder of the mixture is then subjected to a multi-stage liquid extraction in approximately five theoretical stages using water as an extractant. Ethylamines comprising mono, di- and triethylamines are representative of the alkylamines separated by the process.

SUMMARY OF THE INVENTION

This invention relates to an improved process for the distillation separation of methoxyisopropylamine (MOIPA) from a methoxyisopropylamine-water-forming mixture azeotrope. In the process the mixture of methoxyisopropylamine, methyisopropyl alcohol and water is initially distilled at an elevated pressure to form a second water-methoxyisopropylamine azeotrope and a water free bottoms product. The essential feature is that the pressure in the initial distillation is selected such that substantially all of the water is removed as an overhead leaving a water-free bottoms comprising methoxyisopropyl alcohol and methoxyisopropylamine. The overhead from the initial distillation then is subjected to a second distillation generating a bottoms fraction consisting essentially of water and an overhead fraction consisting of methoxyisopropylamine and a small amount of water. This overhead fraction then can be recycled back to the initial distillation or to the initial reaction zone. The bottoms fraction is fractionated in a product column generating an overhead fraction consisting of anhydrous methoxyisopropylamine, and a bottoms fraction containing methoxyisopropyl alcohol and small amount of other by-products.

An advantage of the process described herein is that methoxyisopropylamine can be obtained in essentially anhydrous state without undue processing. Prior processes have been generally unable to generate such anhydrous methoxyisopropylamine product.

BRIEF DESCRIPTION OF THE DRAWING

The drawing is a block flow diagram of a process for producing methoxyisopropylamine by the reaction of methoxyisopropanol and ammonia including the distillation train for recovery of methoxyisopropylamine from the reaction product.

DETAILED DESCRIPTION OF THE INVENTION

Referring to the drawing, methoxyisopropanol. e.g., 1-methoxy-2-propanol, and ammonia are charged via line 1 to reactor 2 which is a fixed bed catalytic reactor containing a conventional catalyst for effecting amination of the alcohol under amination conditions. Typically these aminations will require a pressure of 200 to 300 psig and a reaction temperature of 150 to 230° C. A nickel or cobalt catalyst is often used as the catalyst and hydrogen is added to maintain the catalyst in an active state. The reaction product comprises a mixture of methoxyisopropylamine, unreacted methoxyisopropanol, ammonia, methanol, isopropylamine, water, and impurities which include low boiling organics. The reaction product is removed via line 4 wherein it is charged to ammonia column 6 for removal of ammonia. Ammonia column 6 is operated at a pressure from about 10 to 30 atmospheres and ammonia is removed as an overhead which then can be recycled to the reaction zone.

The bottoms fraction from ammonia column 6 is removed via line 10 and charged to impurities column 12 for removal of low boiling impurities. The low boiling impurities such as methanol and isopropylamine are removed at this point as they can interfere with the separation of water from a methoxyisopropylamine-water azeotrope. Impurities distillation column 12 is operated at pressure ranging from about 20 to 100 psig.

although pressure is not a critical parameter in this operation. The low boiling impurities comprising methanol and methylisopropylamine are removed as an overhead fraction via line 14.

The bottoms fraction which comprises unreacted methoxyisopropanol, methoxyisopropylamine, and water is removed from impurities column 12 via line 16 for separation. Separation is accomplished by removing the bottoms fraction via line 16 and charging the bottoms fraction to distillation column 18. Initial distillation in distillation column 18 is conducted at an elevated pressure ranging from about 100 to 150 psig and preferably at about 110–130 psig. The key to this distillation is the elevation and adjustment of pressure such that the bottoms fraction is essentially water free. The composition in the bottoms fraction consists essentially of methoxyisopropylamine and methoxyiso- propanol. This mixture is then removed from initial distillation column 18 via line 20 and then is distilled in product distillation column 22 generating an overhead fraction consisting essentially anhydrous methoxy- isopropylamine fraction and a bottoms fraction consisting essentially of methoxyisopropyl alcohol. A small amount, e.g., from about 2 to 6% methoxyisopropylamine is lost with the bottoms fraction which is removed from distillation column 22 via line 26.

To recover the balance of the methoxyisopropylamine, the overhead fraction from initial distillation column 18 is charged to distillation column 28 via line 30. A small amount of sodium hydroxide is injected into line 30 prior to distillation in order to maintain an alkaline pH. The composition of the methoxyisopropylamine is essentially that of a second azeotrope comprising about 30% water and 68% methoxyisopropylamine; the balance is methoxyisopropyl alcohol and other impurities. Distillation column 28 is operated at substantially reduced pressure, e.g., 100 to 500 millimeters mercury (mm Hg) and preferably about 180 to 220 millimeters mercury, whereby a bottoms fraction consisting essentially of water is generated. The water fraction is removed via line 34 and discarded from the process. The overhead containing a small fraction of water e.g., from about 2 to 5% and the balance methoxyisopropylamine is removed via line 36 with a portion being returned via line 38 to distillation column 18 and the balance being returned via line 40 to the reaction zone inlet via line 1.

The following examples are provided to illustrate various embodiments of the invention and are not intended to restrict the scope thereof.

EXAMPLE 1

Methoxyisopropylamine was prepared in a conventional manner by reacting ammonia with methoxyisopropyl alcohol in the presence of hydrogen and a nickel catalyst. A reaction product containing methoxyisopropylamine, methanol, isopropylamine, unreacted methylisopropyl alcohol, water and the like was generated.

The reaction product was subjected to a series of distillations. Table 1 below sets forth the components and distillation conditions and feed stream compositions for the distillation process. Compositions are expressed as weight percent and the pressure is in pounds per square inch, gauge or millimeters mercury.

TABLE 1

| Stream No. | 8 | 10 | 14 | 16 | 20 | 24 | 26 | 30 | 34 | 36 | Col 18 | Col 22 | Col 28 |
|---|---|---|---|---|---|---|---|---|---|---|---|---|---|
| NH₃ | 100 | <0.1 | — | — | — | — | — | — | — | — | — | — | — |
| H₂O | — | 12.2 | 4.0 | 14.2 | — | — | — | 36.8 | 100 | 4 | — | — | — |
| MIPA | — | 1.2 | 53.1 | — | — | — | — | — | — | — | — | — | — |
| MEOH | — | 0.7 | 30.9 | — | — | — | — | — | — | — | — | — | — |
| MOIPA | — | 58.4 | 12 | 59.6 | 54.3 | 99.8 | 4 | 67.0 | <0.1 | 96 | — | — | — |
| MOIPOH | — | 26.7 | — | 25.3 | 45.7 | 0.2 | 96 | 2.2 | — | — | — | — | — |
| Other | — | <0.1 | — | — | — | — | — | — | — | — | — | — | — |
| Pressure | — | — | — | — | — | — | — | — | — | — | 120 psig | — | 200 mmHg |

The example shows that the bottoms fraction (stream 20) from the initial distillation column is water-free. At this point, a fraction of the methoxyisopropylamine-water azeotrope has been broken, thereby allowing recovery of a major portion of the methoxyisopropylamine as a water-free product. The balance of the methoxyisopropylamine is recovered by performing a second distillation such that a water fraction essentially free of organic material is generated. This five-stage distillation, therefore, permits recovery of anhydrous methyoxyisopropylamine product and permits removal of water generated in the system.

What is claimed is:

1. In a process for the separation and recovery of an amine from an amine-water azeotrope forming mixture by distillation, the improvement for effecting separation and recovery of methoxyisopropylamine from a low boiling impurity free azeotropic forming mixture comprising methoxyisopropylamine, methoxyisopropyl alcohol and water which comprises:

initially distilling the mixture in an initial distillation zone at an elevated pressure under conditions such that an essentially water-free bottoms fraction consisting essentially of methoxyisopropylamine and methoxyisopropyl alcohol and an overheads fraction consisting of a methoxyisopropylamine-water azeotrope are generated;

distilling the essentially water free bottoms fraction from the initial distillation in a product distillation column generating an overhead fraction consisting of anhydrous methoxyisopropylamine and a bottoms fraction consisting of methoxyisopropyl alcohol;

recovering the methoxyisopropylamine generated as an overhead fraction from the product distillation column;

fractionally distilling the overhead from the initial distillation zone in a second distillation zone at a reduced pressure such that an essentially organic free bottoms fraction and an overhead fraction consisting of methoxyisopropyl amine and water are generated; and removing the organic free bottoms fraction consisting essentially of water and the overhead fraction consisting of methoxyisopropylamine and water from the column.

2. The process of claim 1 wherein the initial distillation is carried out at a pressure of from 100 to 150 psig.

3. The process of claim 2 wherein the initial distillation is carried out at a pressure of about 110–130 psig.

4. The process of claim 2 wherein the distillation of the overhead from the initial distillation is carried out at a pressure ranging from about 100 to 500mm Hg.

5. The process of claim 4 wherein the distillation of the overhead from the initial distillation zone is carried out at a pressure of about 180–220 mm Hg.

6. In a process for the preparation of a purified methoxyisopropylamine product wherein methoxyisopropanol is reacted with ammonia under amination conditions to form a crude methoxyisopropylamine in water reaction product and the methoxyisopropylamine recovered therefrom, the improvement for obtaining essentially anhydrous methoxyisopropylamine which comprises:

a) distilling unreacted ammonia from said crude reaction product; and obtaining a crude methoxyisopropylamine;

b) distilling low boiling impurities from said crude methoxyisopropylamine and removing an azeotrope forming mixture of methoxyisopropylamine, methoxyisopropyl alcohol and water;

c) initially distilling the mixture in an initial distillation zone at an elevated pressure under conditions such that an essentially water-free bottoms organic fraction consisting of methoxyisopropylamine and methylisopropyl alcohol and an overheads fraction consisting of a methoxyisopropylamine-water azeotrope are generated;

d) distilling the essentially water free bottoms fraction from the initial distillation zone in a product distillation column generating an overhead fraction consisting of anhydrous methoxyisopropylamine and a bottoms fraction consisting of methoxyisopropyl alcohol;

e) recovering the methoxyisopropylamine from the product distillation column as an overhead;

f) removing the bottoms fraction consisting of methoxyisopropyl alcohol from the product distillation column.

g) fractionally distilling the overhead fraction obtained from the initial distillation zone in a second distillation zone at a reduced pressure such that an essentially organic free bottoms fraction and a substantially water free overhead are generated; and h) removing the organic free bottoms fraction consisting of water form the column.

* * * * *